US007166736B2

United States Patent
Bright et al.

(10) Patent No.: US 7,166,736 B2
(45) Date of Patent: Jan. 23, 2007

(54) NEOPENTYLGLYCOL BIS(DIARYL PHOSPHATE) ESTERS

(75) Inventors: Danielle Angrand Bright, New City, NY (US); Ronald L. Pirrelli, Mahopac, NY (US); Anantha Narayanan Desikan, Melville, NY (US)

(73) Assignee: Supresta LLC, Ardsley, NY (US)

( * ) Notice: Subject to any disclaimer, the term of this patent is extended or adjusted under 35 U.S.C. 154(b) by 0 days.

(21) Appl. No.: 10/513,745

(22) PCT Filed: May 6, 2003

(86) PCT No.: PCT/US03/14146

§ 371 (c)(1),
(2), (4) Date: Feb. 21, 2006

(87) PCT Pub. No.: WO03/095463

PCT Pub. Date: Nov. 20, 2003

(65) Prior Publication Data

US 2006/0183932 A1    Aug. 17, 2006

(51) Int. Cl.
*C07F 9/02*    (2006.01)

(52) U.S. Cl. .......................... 558/70; 558/147; 558/146
(58) Field of Classification Search ................ 558/70, 558/147, 146
See application file for complete search history.

(56) References Cited

U.S. PATENT DOCUMENTS 6,717,005 B1 * 4/2004 Burkhardt et al. .......... 558/146

* cited by examiner

*Primary Examiner*—Joseph K. McKane
*Assistant Examiner*—Robert Shiao
(74) *Attorney, Agent, or Firm*—Dilworth & Barrese LLP

(57) ABSTRACT

Neopentyl glycol bis(diphenyl phosphate) liquid compositions are described that comprise from about 75% to about 90%, by weight, of neopentyl glycol bis(diphenyl phosphate), less than about 5% by weight of cyclic product, less than about 8% by weight of triphenyl phosphate, and with a $P_3$ content of no less than about 1%, by weight. These compositions are made by continuously adding neopentyl glycol to a diaryl chlorophosphate mixture at elevated temperature, under vacuum, and in the presence of a catalyst.

14 Claims, No Drawings

NEOPENTYLGLYCOL BIS(DIARYL PHOSPHATE) ESTERS

The synthesis of neopentyl glycol bis(diphenyl phosphate) by reaction of neopentyl glycol with diphenyl chlorophosphate in the presence of a Lewis acid catalyst and a liquid hydrocarbon to remove the HCl evolved and decrease the reaction temperature in order to avoid the formation of by-products is described in U.S. Pat. No. 6,136,997. This process suffers from the fact that low temperatures are required to decrease cyclic and triphenyl phosphate by-products formation thus leading to long reaction times for reaction completion.

We have found that the reaction time can be considerably decreased without causing an increase in by-product formation by adding the neopentyl glycol continuously to the DPCP mix at elevated temperature in the presence of a Lewis catalyst and under vacuum. The cycle time, for example, is reduced from seventeen hours to five to seven hours, which is a significant difference.

In U.S. Ser. No. 374,716, filed Jul. 3, 1989, the synthesis of neopentyl glycol bis(diphenyl phosphate) is described employing the reaction of high purity diphenyl chlorophosphate (99% purity) with neopentyl glycol in diethyl ether at 0° C. in the presence of diethyl ether as a solvent. The product obtained by this method was analyzed by $^{31}$P NMR and assayed at 97.5% by weight of neopentyl glycol bis(diphenyl phosphate) with small amounts of by-products (0.57% triphenyl phosphate, 0.32% of cyclic compound, 0.55% of half-ester and 1% of diphenyl acid phosphate). Although neopentylglycol bis(diphenyl phosphate) is obtained in high yield and purity by this method, the approach described is impractical since it involves the use of low temperature, a flammable solvent, and an acid acceptor that has to be recycled.

U.S. Pat. No. 5,041,596, describes the synthesis of neopentyl glycol bis(diphenyl phosphate) from tetraphenyl pyrophosphate and 3,3-dimethyl oxetane in the presence of pyridine at 80° C. under nitrogen. The product obtained by this procedure assayed at 92% by $^{31}$P NMR and contained low levels of cyclic (0.46%), half-ester (2.5%), TPP (1.8%), pyrophosphate species (1.64%). A drawback of this method is its use of a raw material (3,3-dimethyl oxetane) that is only available in research quantities.

The diphenyl chlorophosphate mixture that is used in the process of the present invention contains a predominant amount of diphenyl chlorophosphate (over 90%) and a smaller amount of monophenyl dichlorophosphate and triphenyl phosphate. The amount of monophenyl dichlorophosphate is 5% or less, preferably 2% or less. The amount of triphenyl phosphate is 15% or less, preferably 8% or less, most preferably 5% or less. The presence of the monophenyl dichlorophosphate will cause formation of cyclic by-product and P$_3$ (the triphosphate component of the composition) as shown in Equation 1 riphenyl phosphate of the DPCP mix will be part of the final product (The abbreviation "Ph" in the following Equations means "phenyl")"

Equation 1:

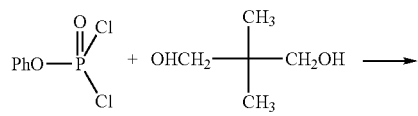

-continued

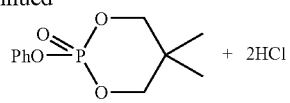

However, additional cyclic and triphenyl phosphate are produced during the reaction according to the following side-reactions:

Equation 2:

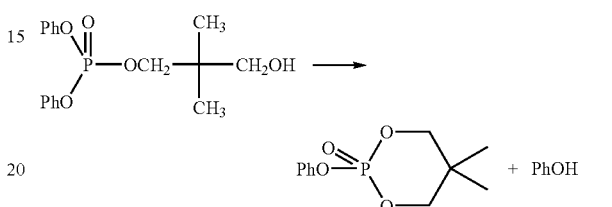

Equation 3:

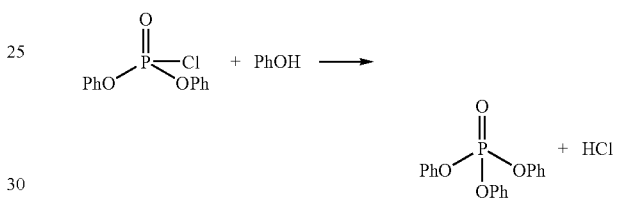

The cyclic product is a solid and has a tendency to crystallize. In order to obtain a liquid product, it is important to keep the level of cyclic by-product in the product below 10% by weight, preferably below 5%. Because triphenyl phosphate is a known cholinesterase inhibitor, it is also important to keep its level in the final product below 10% by weight and preferably below 5% by weight. The phosphate esters of this invention also contain a P$_3$ component. It is believed that the presence of the P$_3$ component helps to keep the mixture liquid.

The preferred catalyst for use in the present invention is magnesium chloride, although other known Lewis acid catalysts can be employed. The amount of catalyst used is generally from about 200 ppm to about 3000 ppm, based on the weight of the DPCP mix. The temperature should be kept within the range of from about 80° C. to about 180° C., preferably from about 130° C. to about 160° C., most preferably about 120° C. to about 150° C. The phosphate esters of this invention, after washing and neutralization, will have an acid number less than about 1.0 mg. KOH/g., preferably less than about 0.10 mg. KOH/g.

The present invention, in one embodiment, provides a method to make neopentylglycol bis(diphenyl phosphates) by a semi-continuous process in which neopentyl glycol is continuously added to a diaryl chlorophosphate mixture at elevated temperature and under vacuum to produce a neopentyl glycol bis(diphenyl phosphate) liquid composition comprising from about 75% to about 90%, by weight, of neopentyl glycol bis(diphenyl phosphate), less than about 5% by weight of cyclic product, less than about 8% by weight of triphenyl phosphate, and with a P$_3$ content of no less than about 1%, by weight.

Another embodiment of the present invention provides a method of producing neopentylglycol bis(diphenyl phosphate) in a continuous process wherein neopentyl glycol and the DPCP mix are continuously reacted to produce a neopentyl glycol bis(diphenyl phosphate) liquid composition having the same composition as described in the previous paragraph.

The following Examples illustrate several embodiments of the present invention.

General Procedure

Run No. 3 in the Table below used the following procedure: To a diphenyl chlorophosphate (DPCP) mixture comprising 93.7% DPCP, 2.47% MPCP (monophenyl dichlorophosphate), and 3.94% TPP (triphenyl phosphate) and a magnesium chloride catalyst (0.96 g), heated under vacuum (as described in the Table), was continuously added neopentyl glycol (238 g, 2.28 moles) under vacuum and over 1.8 hours. At the end of the addition, the reaction mixture was held at the same high temperature for 3.6 hours.

Other Examples were run under different conditions of temperature, pressure, addition time, catalyst level and the results are compiled in Table 1:

NDP will be washed in either the batch or continuous process embodiments employing, for example, an initial water to product weight ratio of 1:1. The wet NDP is then dried under vacuum to give, for example, 609.7 g. of dry neopentyl glycol bis(diphenyl phosphate) having an acid number of under 0.1 mg. KOH/g. The level of cyclic in the final product will typically decrease by 50% during washing.

We claimed:

1. A neopentylglycol bis(diphenyl phosphate) liquid composition comprising from about 75% to about 90%, by weight, of neopentylglycol bis(diphenyl phosphate), less than about 5% by weight of cyclic product, less than about 8% by weight of triphenyl phosphate, and with a $P_3$ content of no less than about 1% by weight.

2. A method of making a neopentylglycol bis(diphenyl phosphate) composition as claimed in claim 1 by a semi-continuous process in which neopentyl glycol bis(diphenyl phosphate) is continuously added to a diaryl chlorophosphate mixture at elevated temperature.

TABLE 1

| Run # | T [° C.] | P [mmHg] | MgCl$_2$ [ppm] | Addition Time [Hrs] | Post Addition Rxn [Hrs] | Feed DPCP Mix [wt %] | | | Product P2 [w %] | P3 wt % |
|---|---|---|---|---|---|---|---|---|---|---|
| | | | | | | MPCP | DPCP | TPP | | |
| 1 | 80  | 55  | 794  | 4.0 | 17.0 | 2.2 | 93.7 | 3.9 | 84.2 | 0.6 |
| 2 | 120 | 55  | 780  | 3.0 | 10.0 | 2.1 | 93.7 | 4.1 | 85.4 | 1.1 |
| 3 | 140 | 55  | 793  | 1.8 | 3.6  | 2.1 | 93.7 | 4.1 | 85.0 | 1.9 |
| 4 | 160 | 55  | 795  | 1.8 | 4.0  | 2.1 | 93.7 | 4.1 | 85.9 | 1.8 |
| 5 | 140 | 100 | 792  | 2.2 | 1.2  | 2.0 | 94.1 | 3.8 | 81.4 | 1.3 |
| 6 | 140 | 55  | 1371 | 3.4 | 2.5  | 2.2 | 92.3 | 5.6 | 85.3 | 2.0 |
| 8 | 120 | 40  | 2000 | 4.0 | 3    | 5.2 | 90.4 | 4.4 | 87.0 | 1.9 |

| Run # | HE wt % | TPP wt % | Product Cyclic [wt %] | Product Phenol [wt %] | Product DPCP [wt %] | Excess Cyclic [wt %] | Excess TPP [wt %] | Excess Phenol [wt %] |
|---|---|---|---|---|---|---|---|---|
| 1 | 0.0  | 7.3 | 4.1 | 3.5  | 0.3  | 1.8 | 3.4 | 3.3 |
| 2 | 0.1  | 6.5 | 6.1 | 0.7  | 0.0  | 4.1 | 2.7 | 0.6 |
| 3 | 0.0  | 6.9 | 4.6 | 0.3  | 1.3  | 2.8 | 2.9 | 0.1 |
| 4 | 0.1  | 7.4 | 4.4 | 0.3  | 0.1  | 2.5 | 3.4 | 0.2 |
| 5 | 0.8  | 6.6 | 6.0 | 0.8  | 3.0  | 4.1 | 2.9 | 0.7 |
| 6 | 0.1  | 7.7 | 4.0 | 0.1  | 0.7  | 2.0 | 1.9 | 0.1 |
| 8 | 0.65 | 5.3 | 3.1 | 0.26 | 0.06 | 2.5 | 1.2 | 0.1 |

The quality of the crude reaction product is a function of temperature, vacuum and catalyst level. The best conditions are those where the crude reaction contained the lowest excess of TPP, cyclic and phenol.

Purification of Final Product:

The crude NDP was washed to remove magnesium, phenol and reduce the acid number. The washing procedure consisted of the steps described in the Table that follows:

| | Type of wash | Temp. |
|---|---|---|
| 1 | Oxalic acid (pH 2) (1%) | 80° C. |
| 2 | NaOH (2% wt) | 65° C. |
| 3 | NaOH (2% wt) | 65° C. |
| 4 | Demineralized water | 65° C. |
| 5 | Demineralized water | 65° C. |

3. A method to produce neopentylglycol bis(diphenyl phosphate) composition as claimed in claim 1 by a continuous process in which neopentyl glycol and the diphenyl chlorophosphate (DPCP) mix are continuously reacted at elevated temperature.

4. A composition according to claim 1, wherein the $P_3$ content is no less than 3% by weight.

5. A process for forming a neopentylglycol bis(diphenyl phosphate) liquid composition as claimed in claim 1 comprising the continuous addition of neopentyl glycol to diphenyl chlorophosphate mix containing 90% or more of diphenyl chlorophosphate, 3% or less monophenyl dichlorophosphate and 5% or less triphenyl phosphate at elevated temperature, under vacuum, and in the presence of a catalyst.

6. A process for forming a neopentylglycol bis(diphenyl phosphate) liquid composition as claimed in claim 1 in which neopentyl glycol and a diphenyl chlorophosphate mix containing 90% or more of diphenyl chlorophosphate, 3% or less monophenyl dichlorophosphate and 5% or less triphenyl phosphate are continuously reacted at elevated temperature, under vacuum and in the presence of a catalyst.

7. A process according to claim 5 where the catalyst is a Lewis acid catalyst.

8. A process according to claim 2 where the elevated temperature is from about 120 to about 180° C.

9. A process according to claim 5 wherein the catalyst is magnesium chloride.

10. A process according to claim 3 where the elevated temperature is from about 120 to about 180° C.

11. A process according to claim 5 where the elevated temperature is from about 120 to about 180° C.

12. A process according to claim 6 where the elevated temperature is from about 120 to about 180° C.

13. A process according to claim 6 wherein the catalyst is magnesium chloride.

14. A process according to claim 7 wherein the catalyst is magnesium chloride.

* * * * *